(12) United States Patent
Jayne et al.

(10) Patent No.: US 6,990,373 B2
(45) Date of Patent: Jan. 24, 2006

(54) AUTOMATED EXTERNAL DEFIBRILLATOR WITH USER INTERFACE FOR ADULT AND PEDIATRIC APPLICATIONS

(75) Inventors: Cynthia P. Jayne, Redmond, WA (US); Richard C. Nova, Kirkland, WA (US); Paula Lank, Renton, WA (US); John C. Daynes, Redmond, WA (US); Anthony J. Santolla, Kirkland, WA (US); Patricia O'Hearn, Mercer Island, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 385 days.

(21) Appl. No.: 10/121,442

(22) Filed: Apr. 10, 2002

(65) Prior Publication Data

US 2003/0195567 A1    Oct. 16, 2003

(51) Int. Cl.
*A61N 1/39* (2006.01)
(52) U.S. Cl. .............................. 607/5; 607/8
(58) Field of Classification Search .............. 607/1–28
See application file for complete search history.

(56) References Cited

U.S. PATENT DOCUMENTS

| | | | |
|---|---|---|---|
| 5,674,253 A | 10/1997 | Adams et al. | |
| 5,817,151 A | 10/1998 | Olson et al. | |
| 6,101,413 A | 8/2000 | Olson et al. | |
| 6,125,298 A | 9/2000 | Olson et al. | |
| 6,134,468 A | 10/2000 | Morgan et al. | |
| 6,370,428 B1 * | 4/2002 | Snyder et al. | 607/5 |
| 6,697,671 B1 * | 2/2004 | Nova et al. | 607/5 |

* cited by examiner

Primary Examiner—Scott M. Getzow
(74) Attorney, Agent, or Firm—Shumaker & Sieffert, P.A.

(57) ABSTRACT

An automated external defibrillator automatically determines the type of patient to which it is attached based on patient-specific information entered by the user. The defibrillator includes electrodes that are adapted for placement on a patient, a pulse generator connected to the electrodes, and processing circuitry that controls the defibrillation pulse delivery from the pulse generator. The automated external defibrillator causes a defibrillation pulse to be delivered to the patient in accordance with the determined patient type. A user interface having a user input connected to the processing circuitry enables the user of the defibrillator to enter patient-specific information. The user may enter the patient-specific information by interacting with the user input during a time period in relation to a prompt from the defibrillator. In another aspect, data pertaining to identification of the type of patient connected to the electrodes may be recorded with event data in a memory.

71 Claims, 3 Drawing Sheets

AUTOMATED EXTERNAL DEFIBRILLATOR WITH USER INTERFACE FOR ADULT AND PEDIATRIC APPLICATIONS

FIELD OF THE INVENTION

The present invention relates generally to electrotherapy apparatus, and more particularly, to automated external defibrillators.

BACKGROUND OF THE INVENTION

Ventricular fibrillation is a life-threatening medical condition in which the electrical activity of a person's heart becomes unsynchronized, resulting in a loss of ability of the heart to pump blood into the person's circulation system. Ventricular fibrillation may be treated by applying one or more strong electrical pulses to the person's heart which gives it a chance to reinitiate a synchronized rhythm. The electrical pulse must be delivered within a short time after onset of ventricular fibrillation for the person to have a reasonable chance of survival.

Automated external defibrillators (AEDs) are typically used by first responders, such as police officers, firefighters and EMTs, to resuscitate victims of ventricular fibrillation or other shockable cardiac arrhythmias. AEDs tend to be more lightweight, compact and portable than manual defibrillators. Because first responders typically have less extensive medical training, AEDs are designed with a simple user interface. After attaching the AED electrode pads to the patient, the user instructs the AED to analyze the patient's condition. If the patient is found to have a shockable cardiac rhythm, the user is advised to stand clear while the AED delivers a defibrillation pulse to the patient.

At present, AEDs are designed to treat adult patients and are not recommended for pediatric patients. Present therapy protocols issued by the American Heart Association for AEDs recommend usage on patients of age eight and above. Nevertheless, cardiac arrest can occur in patients less than eight years old. There is, therefore, a desire for AEDs to be capable of treating pediatric patients.

Pediatric patients generally require lower energy levels for defibrillation than adult patients. For an AED to provide reduced defibrillation energies to pediatric patients, the AED must recognize when it is attached to a pediatric patient. Some prior art approaches have suggested providing the user with multiple sets of electrodes designed for use with different patients of different ages or weights. The electrode sets provide an electrical or mechanical indication to the AED that identifies which electrode set has been connected to the AED. However, providing multiple electrode sets of this type increases the overall cost of the AED.

Other approaches in the prior art have suggested providing an energy reduction apparatus that is connected between the AED and the pediatric patient. An AED of this type delivers a defibrillation pulse of adult dosage. For a pediatric patient, however, the energy reduction apparatus reduces the delivered energy to a level presumably appropriate for the pediatric patient. Connecting an energy reduction apparatus as suggested in the prior art requires additional consideration and effort by the user which may delay treatment. It also adds to the complexity and cost of the AED, and is energy inefficient.

Accordingly, there is a need for an AED that can automatically determine whether it is attached to an adult or pediatric patient based on information entered by the user in the course of AED operation. A need further exists for an AED that adjusts its operational aspects, such as energy delivery, for pediatric patients based on the user-entered information.

SUMMARY OF THE INVENTION

In one exemplary embodiment of the present invention, an automated external defibrillator automatically determines the type of patient to which it is attached based on patient-specific information entered by the user. The automated external defibrillator causes a defibrillation pulse to be delivered to the patient in accordance with the determined patient type. Included with the automated external defibrillator are electrodes adapted for placement on the patient. A pulse generator is connected to the electrodes for delivering defibrillation pulses and is controlled by processing circuitry in the automated external defibrillator. A user interface that has a user input connected to the processing circuitry enables the user of the defibrillator to enter the patient-specific information.

In another exemplary embodiment of the invention, the automated external defibrillator may include a user output that prompts the user to enter patient-specific information. The user enters the patient-specific information by interacting with the user input during a time period in relation to the prompt. The user may enter different patient-specific information depending on the time period in which the user interacts with the user input.

Examples of patient-specific information that may be entered by the user include information that reflects a range or an approximate age or weight of the patient. The user input may also comprise a variable-length element that is extendable from the defibrillator or from a separate device. The user enters the patient-specific information by extending the element to approximate a physical distance related to the patient, such as the height of the patient or the length of a limb of the patient.

The processing circuitry in the automated external defibrillator may be configured to determine a defibrillation pulse dosage to be delivered to the patient based on the determined patient type. The processing circuitry may also determine a defibrillation therapy protocol based on the patient determination.

In yet further embodiments of the invention, the user input may be comprised of two or more separate ports in the automated external defibrillator for connecting electrodes to the defibrillator. The patient-specific information may be communicated by the user to the processing circuitry by virtue of the port to which the user connects the electrodes. For example, one port may be designated for connecting the electrodes to a pediatric patient and another port may be designated for connecting the electrodes to an adult patient.

The automated external defibrillator may also receive the patient-specific information from an external device, either by wireless or wired communication. Voice recognition capabilities are further possible with the present invention wherein the user enters the patient-specific information by speaking into a microphone in communication with the defibrillator.

The patient type determination may be made by the processing circuitry in the defibrillator or by a separate processing unit that may be elsewhere in the defibrillator (e.g., in the defibrillator's user interface). Likewise, the determination of an electrotherapy dosage or electrotherapy protocol may be made by either the processing circuitry of the defibrillator or by a separate processing unit in the user interface or the pulse generator.

In another aspect of the present invention, data pertaining to identification of the type of patient connected to the electrodes may be recorded with event data in a memory. Event data generally includes data related to the defibrillator's evaluation of the patient and delivery (if any) of defibrillation therapy. Recording the patient type with the event data provides further information about the patient for later evaluation.

The present invention also contemplates an automated external defibrillator that adjusts therapy delivery and/or event data recording based directly on the user-entered patient-specific information.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

An automated external defibrillator ("AED") constructed in accordance with the present invention receives patient-specific information from a user of the defibrillator during the course of operating the defibrillator. The patient-specific information entered by the user enables the AED to determine the type of patient to which it is connected (e.g., an adult or pediatric patient.) The AED may automatically determine the dosage for a defibrillation pulse to be delivered to the patient based on the patient determination. The AED may also automatically modify the information output to the user based on the patient determination.

Figure 1:
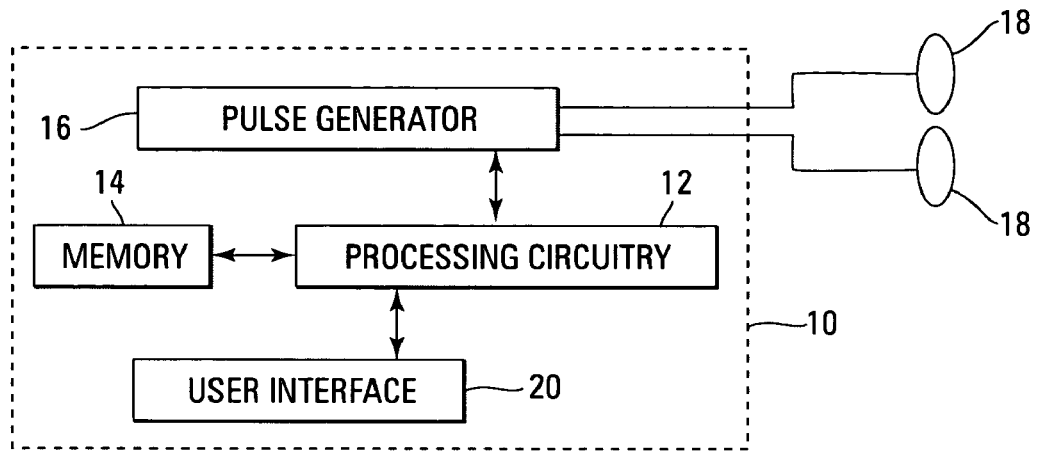
FIG. 1 is a block diagram of an automated external defibrillator constructed in accordance with the present invention showing major components thereof.

FIG. 1 is a block diagram of an AED 10 constructed in accordance with the present invention. The AED 10 includes processing circuitry 12 in communication with a memory 14. The processing circuitry 12 may include one or more integrated circuits (e.g., microprocessors) or other electronic circuitry capable of controlling the operation of the AED 10. Embodiments of the invention using digital components for the processing circuitry 12 preferably operate in accordance with programmed instructions stored in the memory 14.

The processing circuitry 12 controls the overall operation of the AED 10, including the delivery of defibrillation therapy to patients. In communication with the processing circuitry 12 is a pulse generator 16 that is configured to deliver defibrillation therapy to a patient via electrodes 18 that are placed on the patient.

The pulse generator 16 may include conventional components for generating and delivering defibrillation pulses. In that regard, the pulse generator 16 generally includes an energy source (e.g., a battery), an energy storage device, (e.g., a capacitor), and a switch. When defibrillation therapy is to be delivered via the electrodes 18, the pulse generator 16 uses the energy source to charge the energy storage device to a desired level. The switch in the pulse generator 16 is then operated to connect the energy storage device to the electrodes 18, thereby permitting the energy in the energy storage device to flow from one electrode 18 through the patient to the other electrode 18. In embodiments where a multiphasic defibrillation pulse is delivered to the patient, the switch may be operated to reverse the flow of energy through the patient after an initial energy pulse is delivered to the patient.

The operation of the switch may be controlled by processing circuitry in the pulse generator 16 or by other processing circuitry, such as the AED's processing circuitry 12. The charging operation of the energy storage device may also be controlled by processing circuitry in the pulse generator 16 or by the AED's processing circuitry 12.

As will be discussed further below, the pulse generator 16 is preferably configured to permit the processing circuitry 12 to receive ECG signals and/or other patient signals (heart sounds, patient impedance signals, etc.) sensed by the electrodes 18. The processing circuitry 12 analyzes the ECG signals, for instance, to determine whether a cardiac rhythm treatable by defibrillation therapy is present in the patient.

After attaching the electrodes 18 to a patient (which electrodes may be selected from one or more electrode sets provided for use with the AED 10), a user of the AED 10 enters information into the AED that is specific to the patient to which the AED 10 is connected. A preferred embodiment of the AED 10, therefore, includes a user interface 20 configured to receive the patient-specific information from the user.

Figure 2:
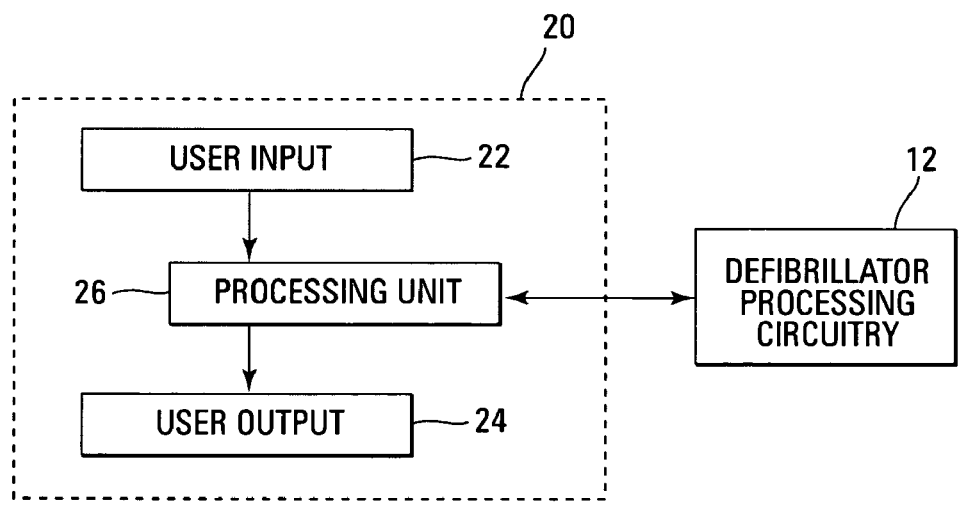
FIG. 2 is a block diagram showing major components of a user interface as illustrated in FIG. 1.

One exemplary embodiment of the user interface 20 is illustrated in FIG. 2. In FIG. 2, the user interface 20 includes a user input 22 and a user output 24, both of which are in communication with a processing unit 26. The processing unit 26 is preferably configured to communicate information to and from the AED's processing circuitry 12.

The user input 22 may be comprised of one or more conventional input devices, such a button, key, knob, switch, and the like. The user input 22 may be a single such device, or it may include a plurality of such devices. The user input 22 may also include an external device that inputs information to the AED 10 via an input port in the AED, or via a wireless or hardwired connection to the AED. In any regard, during the course of operating the AED 10, the user of the AED interacts with the user input 22 to provide the AED with information that is specific to the patient. In a preferred embodiment, the patient-specific information reflects the magnitude of a physical attribute of the patient. This information may include, by nonlimiting example, an approximate age or weight of the patient. The patient-specific information may also be provided as a range, such as an age range or weight range of the patient. Depending on the patient-specific information entered by the user, the AED determines whether the patient is an adult or pediatric patient. The AED may use a preprogrammed algorithm that classifies patients under a certain age or weight (e.g., <8 years old or 25 kg) as "pediatric" patient type and all other patients as "adult" patient type. Other ages or weights (or ranges thereof) may be used. The present invention also contemplates an AED using more than two patient types to classify the patient.

Figure 3:
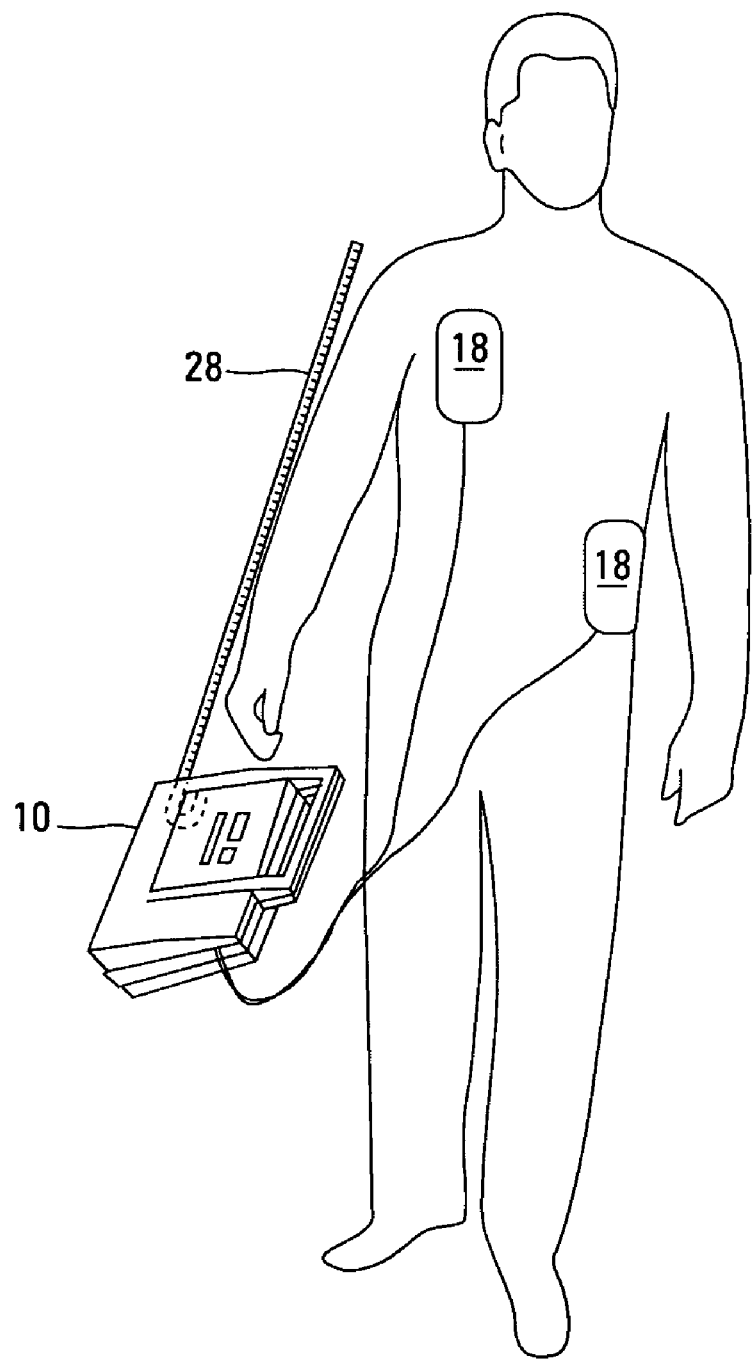
FIG. 3 is a pictorial diagram of an automated external defibrillator including a variable-length element that extends from the defibrillator to measure a physical distance related to a patient in accordance with the present invention.

Other types of patient-specific information may be entered by the user. For example, the patient-specific information may be a measurement of a physical distance related to the patient, such as the patient's height, or the length of a limb of the patient. In that regard, the user input 22 may include a variable-length element that is extendable from the AED or from a separate device to measure a physical distance. For example, FIG. 3 depicts the AED 10 with a retractable tape 28 that has been extended to measure the length of a patient's arm. The retractable tape 28 may operate in a manner similar to the Broselow tape system used for pediatric emergency medicine. In the Broselow tape system, a tape measure is divided into several color-coded lengths. Each length class has predefined dosages for medicines and sizes for intubation devices, catheters, etc. When the tape 28 is extended from the AED 10 to measure the length or height of the patient's body or limb thereof, markings on the tape 28 provide information to the user that the user may then enter into the AED. The AED 10 may also be advantageously configured with optical or electrical sensors that automatically detect the final length of the tape 28 that has been extended from the AED. Depending on the final length of the tape 28, the AED 10 may automatically determine whether the patient is an adult or pediatric patient and modify its operation accordingly. The determination of the patient as an adult or pediatric patient may rely on standard human growth charts that relate a height or length of the patient to an expected age or weight. In implementations where the variable-length element is extendable from a separate device, the device is preferably configured to communicate the length of the element to the AED, by either wired or wireless communication, when the element has been extended.

Returning to FIG. 2, the patient-specific information entered by the user via the user input 22 is communicated to the processing unit 26 of the user interface 20. The processing unit 26 preferably controls the operation of the user interface 20. The processing unit 26 may also be configured to control other processes in the AED 10. For example, an embodiment of the invention may include a user interface 20 with a processing unit 26 that is configured to automatically determine an electrotherapy dosage to be delivered to the patient based on the patient determination. If the AED has determined the patient to be a pediatric patient, the AED preferably determines a lower electrotherapy dosage (e.g., 50 joules for a defibrillation pulse) to deliver to the patient. If the patient is determined to be an adult, the AED may deliver a higher electrotherapy dosage (e.g., 200 joules) for the patient. The determined defibrillation dosage is then communicated to the AED 10, either to the AED processing circuitry 12 or directly to the pulse generator 16. The processing unit 26 may be further configured to automatically cause the pulse generator 16 to deliver the defibrillation pulse to the patient in accordance with the selected dosage.

In yet another embodiment of the invention, the processing unit 26 or AED processing circuitry 12 may be configured to automatically determine an electrotherapy protocol for the patient based on the patient determination. For example, in circumstances where the AED 10 determines it is connected to an adult patient, the processing circuitry 12 may select a protocol of three defibrillation pulses of pre-determined energy, e.g., 200 joules, 300 joules, and 360 joules, to be delivered to the patient. If the electrotherapy protocol is determined by the user interface processing unit 26, the protocol may be communicated from the processing unit 26 to the AED processing circuitry 12 so that the processing circuitry 12 can control the therapy delivery in accordance with the determined protocol.

The user output 24 may be used in connection with the user input 22 to assist in entry of the patient-specific information. For example, the user output 24 may be used to prompt the user to enter the patient-specific information. The user output 24 may be comprised of conventional components for communicating information, including, for example, a display screen, one or more LEDs, a speaker for audible communication, an output port for signal communication with another device, and/or a printer.

In further embodiments of the invention, the user may enter patient-specific information into the AED 10 by interacting with the user input 22 during a time period in relation to a prompt given to the user via the user output 24. For example, the user output 24 may provide the following prompt to the user: "If patient is less than age 8, press button now." At this point, the user interface 20 waits for the user to interact with the user input (i.e., button) 22. If the user interacts with the user input 22, within a predetermined time period following the prompt, the processing unit 26 in the user interface 20 interprets the user interaction as confirming that the patient is less than 8 years old. If the predetermined time period expires without user interaction with the user input 22, the processing unit 26 may conclude that the patient is age 8 or above. Alternatively, the AED may separately request the user to confirm that the patient is age 8 or above, by interacting with the user input 22. If the user still fails to interact with the user input 22, the AED may either cycle back to the first prompt (patient less than age 8) or immediately conclude the patient is an adult. The information thus received by the processing unit 26 may then be communicated to the AED processing circuitry 12.

In the foregoing example, the designation of age 8 (for pediatric patients) is consistent with current American Heart Association guidelines, but nonetheless is not required. Other embodiments of the invention may prompt the user to interact with the user interface to indicate the patient is of a different age or age range. Furthermore, the user interface 20 may prompt the user for information related to other aspects of the patient, including the patient's approximate weight, height, etc. This information may similarly be entered by giving the user a prompt and permitting the user to respond in a predetermined time period in relation to the prompt.

Multiple prompts may also be used in connection with these embodiments of the invention. For example, the user interface 20 may prompt the user, either verbally or visually, with the following prompt: "If the patient is age 4 or less, press button now." If the user does not interact with the user input 22 within a predetermined time period following this prompt, the user interface 20 may follow up with another prompt, such as: "If patient is between age 4 and age 8, press button now." Other prompts may follow, depending on the user's interaction (or lack of interaction) with the user input 22 following the prompts.

Further embodiments of the invention may include a user input 22 with voice recognition capabilities. Conventional software providing voice recognition may be integrated into the AED 10 to provide a user with a streamlined user interface 20. Generally speaking, voice recognition algorithms typically require a triggering event, such as a spoken trigger word or other user interaction (e.g., turning the AED on), to prepare the AED to receive a voice activated input. Other embodiments of the invention may provide a prompt to the user via the user output 24 to signal the user to provide voice activated input. For example, the AED 10 may visually or audibly ask the user to state the patient's approximate weight, age, or height.

In any regard, following the triggering event or prompt, the AED 10 waits for the user to supply the requested patient-specific information. Various embodiments of the invention may include a microphone integrated with the AED, a microphone configured to attach to the user's body or in a headset that the user places on his or her head. Microphones that are closer to the user will have a better signal-to-noise ratio for filtering out voices and noises of others that are nearby. Battery-powered wireless communication technology may be used to simplify the placement of a microphone on the user. The user then audibly states the patient-specific information, which is recognized and acted on by the AED 10.

Electrodes may also be configured for user selection so that when the electrodes are connected to the AED, an indicator in the electrodes indicates the electrode configuration to the AED. The AED may then determine the patient type based on the user-selected electrode configuration. Examples of electrodes having an indicator to identify the electrode configuration are suitably found in U.S. patent application Ser. No. 10/094,949 titled THERAPY AND MONITORING ELECTRODES WITH PATIENT ACCOMMODATING FEATURES, assigned to the assignee of the present invention, the disclosure of which is incorporated by reference herein. Other commercially-available electrodes having configuration indicators may also be used.

Based on the patient-specific information entered by the user, the AED 10 automatically determines whether the patient to which the AED is connected is an adult or pediatric patient. Where, for example, the patient-specific information is the patient's approximate age (or age range), the AED 10 may determine that the patient is a pediatric patient if the patient's age falls below a predetermined threshold (e.g., <8 years old). Other information received from the user may be similarly processed to determine whether the patient is an adult or pediatric patient. Where the patient-specific information communicates a physical measurement of the patient, such as an approximate weight, height, length, etc., this information may be compared with a predetermined threshold to classify the patient type. For example, if the user enters the patient's approximate weight and it exceeds a predetermined threshold, the AED 10 may conclude that the patient is an adult; otherwise, the AED concludes it is attached to a pediatric patient. The predetermined threshold may be based on standard growth charts that correlate patient size to typical patient age. The AED's determination of whether the patient is an adult or pediatric patient may be communicated to the user via the user output 24.

The AED 10 may take a number of different actions depending on the AED's determination of patient type. In one aspect, the AED 10 may adjust the amount of energy or the duration of defibrillation therapy to be delivered to the patient. Where the patient is a pediatric patient, the AED may automatically scale down the defibrillation therapy to a level appropriate for the pediatric patient. Likewise, if the AED determines it is connected to an adult patient, the AED may continue to deliver defibrillation therapy that is appropriate for an adult.

Interpolation or extrapolation from predetermined energy levels may also be provided. Patient-specific information entered by the user that reflects a particular age or weight (or age range or weight range) may cause the AED 10 to adjust the defibrillation therapy for the indicated age or weight of the patient. In other words, different amounts of energy may be delivered to patients of different age or weight, as appropriate. Other therapy parameters, such as pulse duration, tilt, peak current, or peak voltage for example, may be adjusted for the patient according to the patient-specific information entered by the user.

In another aspect, the AED 10 may modify information that is output to the user, including information communicated via the user output 24, depending on the patient type determined by the AED. The AED 10 may also modify information recorded in the memory 14, such as event data, that is stored for later download and review by the user or by others. Output information that is modified in this respect may include, for example, the amount of energy delivered to the patient. This is particularly advantageous for embodiments of the invention where an adult electrotherapy dosage is generated for all patients but routed through energy reduction circuitry for pediatric patients that reduces the amount of energy actually delivered to the patient. For pediatric patients, the event data reflecting energy delivered would not be based on the adult dosage to which the AED was prepared to deliver, but instead would identify the reduced amount of energy actually delivered to the patient.

Figure 4:
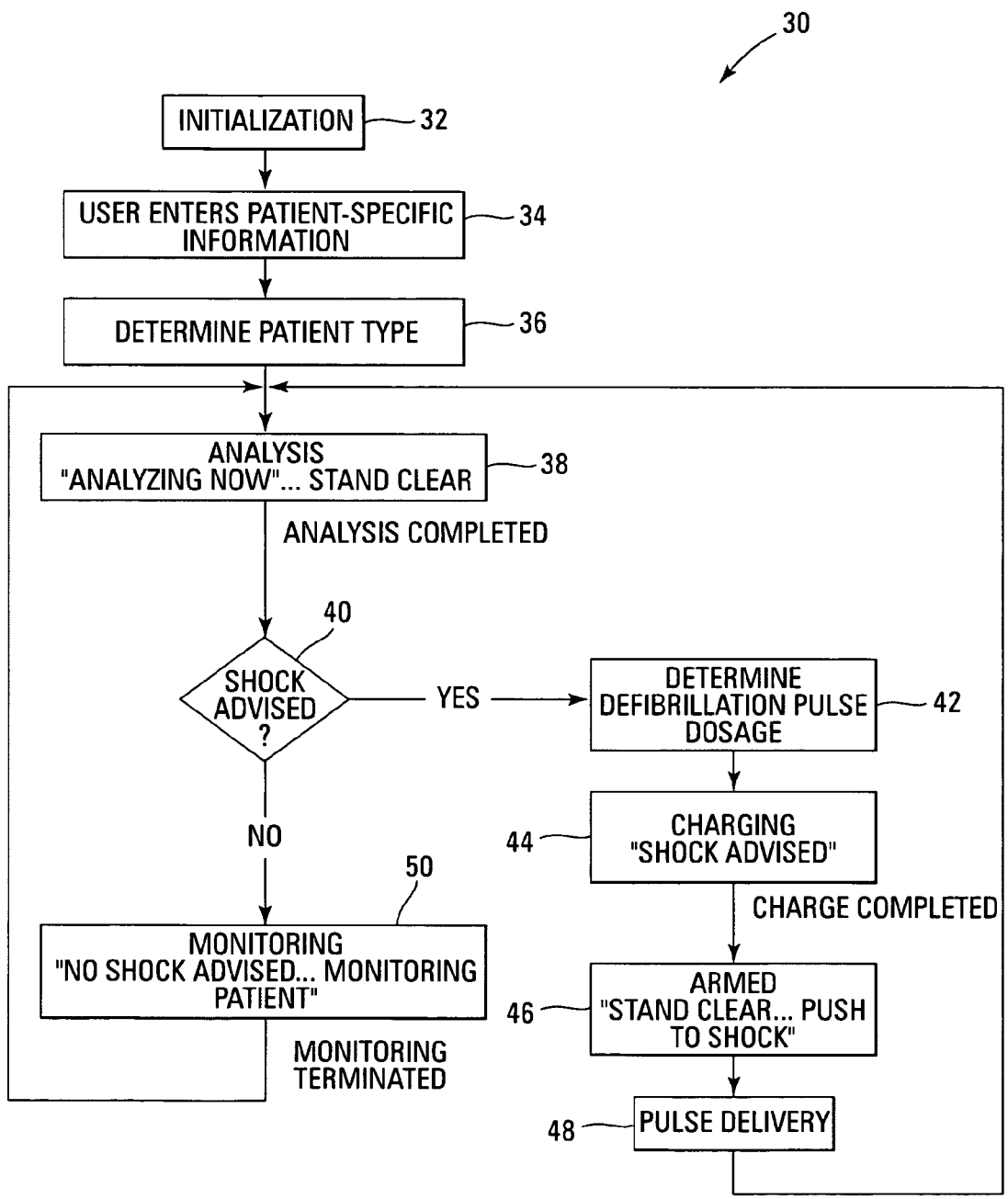
FIG. 4 is a flow diagram illustrating a patient analysis and defibrillation process conducted in accordance with the present invention.

FIG. 4 illustrates an exemplary patient analysis and defibrillation process 30 conducted in accordance with the present invention. At a first block 32, the operation of the AED is initialized. At the same time or shortly thereafter, the defibrillation electrodes 18 of the AED 10 are placed on the patient. Once the electrodes 18 are connected to the AED 10 and attached to the patient, and the AED 10 is ready for operation, the AED receives patient-specific information entered by the user, as indicated at block 34. At block 36, the AED uses the patient-specific information to determine the type of patient being treated, e.g., infant patient, pediatric patient, adult patient, etc.

At block 38, the AED performs an analysis of the patient. In this regard, the AED may obtain various electrical signals and parameters from the patient, including electrocardiogram (ECG) data. ECG signals obtained from the patient via the electrodes 18 may be amplified and filtered in the AED in a conventional manner, and converted into digitized ECG data for evaluation by the AED's processing circuitry 12.

Preferably, the processing circuitry 12 evaluates the patient's ECG signals in accordance with programmed instructions stored in the memory 14 that carry out an ECG evaluation process. The ECG evaluation process determines whether a defibrillation pulse should be provided to the patient. One suitable method for determining whether to apply a defibrillation shock based on a patient's ECG signals is described in U.S. Pat. No. 4,610,254, which is assigned to the assignee of the present invention and the disclosure of which is incorporated by reference herein. Other shock advisory algorithms known in the art may be used in this aspect of the invention.

If, at decision block 40, the processing circuitry 12 determines that delivery of a defibrillation pulse is appropriate, the processing circuitry 12 preferably determines an appropriate dosage of energy to be delivered to the patient, as indicated at block 42. Known algorithms for determining a defibrillation energy dosage may be used. For example, if the patient is determined to be a pediatric patient, the energy delivered may be a predetermined amount of energy, such as 80 joules. The same algorithm may prescribe 25 joules for an infant, while adult patients receive 200 joules in a defibrillation pulse.

Other algorithms may prescribe a percentage of the adult-recommended dosage for pediatric or infant patients, e.g., 35%, which represents a 65% reduction from an adult dosage. Different energy levels may be set for patients of different age, weight, or size, depending on the patient-specific information that is entered by the user. For example, a suitable guideline, such as 2 joules per kilogram (patient weight), may be used to determine the appropriate dosage.

At block 44, the AED 10 prompts the user with a message "Shock advised" and commences charging an energy storage device in the pulse generator 16. The energy storage device is charged to a level that will cause a defibrillation pulse to be delivered to the patient in accordance with the determined defibrillation pulse dosage.

Once the energy storage device is charged, the AED 10 is armed and ready to deliver the defibrillation pulse to the patient, as indicated at block 46. In that regard, the AED 10 may give user the following prompt: "Stand clear . . . Push to shock." At that point, the AED 10 may wait for the user to push a specified button or otherwise interact with the AED to initiate delivery of the defibrillation pulse. (For a fully automatic AED, the pulse is automatically delivered without user intervention; there is no shock button.) In the example provided, once the shock button is pushed, the defibrillation pulse is delivered to the patient, as indicated at block 48. The process 30 may then return to block 38 to reanalyze the patient and determine whether the defibrillation pulse was successful or whether another defibrillation pulse is necessary.

If, at decision block 40, the processing circuitry 12 determines that the patient does not have a shockable cardiac rhythm, and therefore a defibrillation pulse is not advised, the AED 10 may proceed to a monitoring mode, as indicated at block 50, and monitor patient signals, such as the patient's ECG. In the monitoring mode, the AED 10 may prompt the user with: "No shock advised . . . Monitoring patient." The monitoring may continue for a predetermined period of time. Alternatively, the monitoring may continue indefinitely until an anomaly or some other event is detected in the patient's condition. When the monitoring is terminated, the process 30 preferably returns to analyzing the patient's condition as indicated at block 38.

During the monitoring in block 50, the AED 10 may also prompt the user to deliver alternative therapy to the patient. For instance, the AED may prompt the user to commence cardiopulmonary resuscitation (CPR) or deliver one or more drugs (e.g., by injection) to the patient. These user prompts, as well as other prompts provided to the user throughout the operation of the AED, may be modified based on the AED's patient determination or the patient-specific information that is entered by the user. If, for example, the AED 10 has determined from the patient-specific information that the patient is a pediatric patient, the AED may prompt the user with: "Use infant face mask to deliver respiration."

An AED constructed according to the present invention has an advantage of being able to automatically recognize and treat patients of all ages and sizes. The operation of the AED remains simple as the AED determines the type of patient it is treating by using the patient-specific information that is entered by the user in the course of operating the defibrillator. The patient-specific information (or the patient type derived from the patient-specific information) is used by the AED to adjust its operation to address the particular patient being treated.

The patient-specific information may also be used to modify an event recording process in the AED 10. When the AED 10 is attached to a patient for analysis and delivery of electrotherapy, the AED may collect data regarding the event and retain the data in a memory, where it is available for later download and review. In accordance with the present invention, the AED 10 may record with the event data the user-entered patient-specific information (and/or patient type determined from the patient-specific information). This additional information identifies the data as pertaining to an adult or pediatric patient.

The AED 10 may also modify the event data it records based on the patient type determination. For example, an AED may be configured to provide an adult dosage of defibrillation therapy in all cases to all patients. For pediatric patients, however, the user connects an energy attenuator (e.g., resistor) in the circuit path between the AED and the patient, which reduces the amount of energy actually delivered to the patient. Alternatively, the AED 10 may automatically switch a resistor or resistor network into the circuit path with the electrodes once it determines the patient to be a pediatric patient. From the perspective of the AED's energy storage device, it appears that an adult dosage of energy was delivered. However, with the present invention, the AED recognizes when it is attached to a pediatric patient and energy attenuation has occurred. Rather than recording the delivery of an adult-size energy dosage, which in fact did not occur, the AED 10 instead records the reduced amount of energy expected to result from the energy attenuator.

While several embodiments of the invention have been illustrated and described, it will be appreciated that various changes can be made therein without departing from the spirit and scope of the invention. For example, a separate processing unit 26 in the user interface 20 is not required. The user input 22 and user output 24 may be directly connected to the AED's processing circuitry 12. Moreover, it should be understood that the terms "adult" and "pediatric" as used herein are not meant to be limiting to any specific age group or patient size. Rather, the terms "adult" and "pediatric" are indicators of patient types which the AED 10 may determine from the patient-specific information entered by the user. Additional patient types or subtypes, such as "infant," may also be defined within, in addition to, or in place of "adult" and "pediatric" patient types.

Furthermore, embodiments of the invention set forth above describe the AED 10 as modifying aspects of its operation based on the AED's determination of the type of patient to which it is connected. However, it should also be understood that the AED 10 may modify its operation in the manner described above based directly on the user-entered patient-specific information. In that regard, for example, if the user enters information reflecting an estimated age of the patient, the AED 10 may automatically adjust the delivery of defibrillation therapy in accordance with the patient's age, without first determining the patient type from the patient-specific information. The AED 10 may also modify its operation at the same time as determining the patient type from the patient-specific information.

It should also be recognized that the advantages of the present invention may be achieved in a hybrid defibrillator that can selectably operate in manual or AED mode. As with the AED embodiments described above, the hybrid defibrillator may automatically adjust its delivery of defibrillation therapy based on the patient information entered into the defibrillator by the user.

The scope of invention, therefore, should be determined in reference to the following claims and equivalents thereto.

The invention claimed is:

1. An automated external defibrillator that delivers defibrillation therapy to adult and pediatric patients, comprising:
   electrodes that are adapted for placement on a patient;
   a port that connects the electrodes to the defibrillator;

a pulse generator connected to the electrodes, via the port, that delivers a defibrillation pulse to the patient;

processing circuitry connected to the pulse generator that controls the defibrillation pulse delivery; and a user interface including a user input connected to the processing circuitry that enables a user of the defibrillator to enter patient-specific information reflecting the magnitude of a physical attribute of the patient into the defibrillator, wherein the processing circuitry is configured to automatically determine a patient type based on the patient-specific information entered by the user; and cause the pulse generator to deliver a defibrillation pulse to the patient in accordance with the patient type determination.

2. The automated external defibrillator of claim 1, wherein the determined patient type is selected from the group consisting of adult, pediatric, and infant patient types.

3. The automated external defibrillator of claim 1, wherein the user interface includes a user output that prompts the user to enter the patient-specific information, said patient-specific information being entered by user interaction with the user input during a time period in relation to the prompt.

4. The automated external defibrillator of claim 3, wherein the user enters different patient-specific information depending on the time period in which the user interacts with the user input.

5. The automated external defibrillator of claim 3, wherein the user output is further configured to provide multiple prompts and wherein said patient-specific information is entered by user interaction with the user input in time relation to one of the prompts.

6. The automated external defibrillator of claim 1, wherein the patient-specific information entered by the user reflects an approximate age of the patient.

7. The automated external defibrillator of claim 1, wherein the patient-specific information entered by the user reflects an approximate weight of the patient.

8. The automated external defibrillator of claim 1, wherein the user input comprises an extendable variable-length element that is extendable from the defibrillator or from a separate device, and wherein the patient-specific information is entered by the user by extending said element to approximate a physical distance related to the patient.

9. The automated external defibrillator of claim 8, wherein the physical distance is related to a height of the patient.

10. The automated external defibrillator of claim 8, wherein the physical distance is related to a length of a limb of the patient.

11. The automated external defibrillator of claim 1, wherein the processing circuitry is further configured to determine a defibrillation pulse dosage to be delivered to the patient based on the patient type determination and cause the pulse generator to deliver a defibrillation pulse to the patient in accordance with the determined dosage.

12. The automated external defibrillator of claim 1, wherein the processing circuitry is further configured to determine a defibrillation therapy protocol based on the patient type determination and cause the pulse generator to deliver a defibrillation pulse to the patient in accordance wit the determined protocol.

13. The automated external defibrillator of claim 1, wherein the user input is comprised of a microphone and voice recognition circuitry capable of receiving and processing user speech, and wherein the patient-specific information is recognized and entered into the defibrillator from the user's speech.

14. An automated external defibrillator that delivers defibrillation therapy to adult and pediatric patients, comprising:

electrodes that are adapted for placement on a patient;

a first port that connects the electrodes to the defibrillator, a pulse generator connected to the electrodes that delivers a defibrillation pulse to the patient;

processing circuitry connected to the pulse generator that controls the defibrillation pulse delivery; and a user interface including a user input comprised of a second port connected to the processing circuitry that enables a user of the defibrillator to enter patient-specific information representing the magnitude of a physical attribute of the patient into the defibrillator, wherein the processing circuitry is configured to automatically determine a patient type based on the patient-specific information entered by the user; and cause the pulse generator to deliver a defibrillation pulse to the patient in accordance with the patient type determination.

15. The automated external defibrillator of claim 14, wherein the second port receives information from an external device, and wherein the patient-specific information is communicated to the defibrillator from the external device.

16. The automated external defibrillator of claim 15, wherein the second port is a wireless communication port that receives information from the external device via wireless transmission.

17. An automated external defibrillator that delivers defibrillation therapy to adult and pediatric patients, comprising:

(a) electrodes that are adapted far placement on a patient;

(b) a pulse generator connected to the electrodes that delivers a defibrillation pulse to the patient;

(c) processing circuitry connected to the pulse generator that controls the defibrillation pulse delivery; and (d) a user interface including a user input connected to the processing circuitry, wherein the user input is comprised of two or more separate ports in the defibrillator for connecting the electrodes to the defibrillator, and wherein patient-specific information is communicated by the user to the processing circuitry by virtue of the port to which the user connects the electrodes, wherein the processing circuitry is configured to automatically (1) determine a patient type based on the patient-specific information; and (2) cause the pulse generator to deliver a defibrillation pulse to the patient in accordance with the patient type determination.

18. The automated external defibrillator of claim 17, wherein one port is designated for connecting the electrodes to a pediatric patient and another port is designated for connecting the electrodes to an adult patient.

19. A user interface for use with an automated external defibrillator that delivers electrotherapy, the defibrillator including electrodes that are placed on a patient and electrotherapy generating circuitry that delivers the electrotherapy to the patient via the electrodes, and a port that connects the electrodes to the defibrillator, the user interface comprising:

a user input, separate from the port, that enables a user of the defibrillator to enter patient-specific information reflecting the magnitude of a physical attribute of the patient; and a processing unit connected to the user input for receiving the patient-specific information entered by the user, wherein the processing unit is configured to communicate information to and from a processing circuitry, the processing circuitry configured to automatically determine a patient type based on the patient-specific information entered by the user; and communicate the patient type determination to the defibrillator.

20. The user interface of claim 19, further comprising a user output that prompts the user to enter the patient-specific information via the user input.

21. The user interface of claim 20, wherein the patient-specific information depends on the time period in relation to the prompt in which the user interacts with the user input.

22. The user interface of claim 19, wherein the determined patient type is selected from the group consisting of adult, pediatric, and infant patient types.

23. The user interface of claim 19, wherein the processing unit is further configured to automatically determine an electrotherapy dosage to be delivered to the patient based on the patient type determination and communicate the determined dosage to the defibrillator.

24. The user interface of claim 23, wherein the processing unit is further configured to automatically cause the electrotherapy generating circuitry of the defibrillator to deliver electrotherapy to the patient in accordance with the determined dosage.

25. The user interface of claim 19, wherein the processing unit is further configured to automatically determine an electrotherapy protocol for the patient based on the patient type determination and communicate the determined protocol to the defibrillator.

26. The user interface of claim 19, wherein the user input is comprised of a microphone and voice recognition circuitry capable of receiving and processing user speech, and wherein the patient-specific information is recognized and entered into the user input from the user's speech.

27. The user interface of claim 19, wherein the configuration of the electrodes can be modified by the user depending on the type of patient, and wherein the user input is comprised of an indicator in the electrodes that indicates the configuration of the electrodes, the processing unit being further configured to receive the patient-specific information by detecting the configuration of the electrodes via the indicator.

28. A user interface for use with an automated external defibrillator that delivers electrotherapy, the defibrillator including electrodes that are placed on a patient and electrotherapy generating circuitry that delivers the electrotherapy to the patient via the electrodes, and a first port that connects the electrodes to the defibrillator, the user interface comprising:

a user input comprised of a second port that enables a user of the defibrillator to enter patient-specific information representing the magnitude of a physical attribute of the patient into the defibrillator; and a processing unit connected to the user input for receiving the patient-specific information entered by the user, wherein the processing unit is configured to automatically determine a patient type based on the patient-specific information entered by the user; and communicate the patient type determination to the defibrillator.

29. The user interface of claim 28, wherein the port is a wireless communication port that receives the patient-specific information from the external device via wireless transmission.

30. The user interface of claim 29, wherein the port is an electrode port, and wherein the external device is an electronic circuit connected in series between the defibrillator and the electrodes, the electronic circuit being configured to provide the patient-specific information to the defibrillator.

31. The user interface of claim 29, wherein the electronic circuit includes a patient selection control that the user may manipulate to identify the patient type.

32. A user interface for use with an automated external defibrillator that delivers electrotherapy, the defibrillator including electrodes that are placed on a patient and electrotherapy generating circuitry that delivers the electrotherapy to the patient via the electrodes, the user interface comprising:

(a) a user input comprising two or more separate ports for connecting the electrodes to the defibrillator, and wherein patient-specific information is communicated by the user to the processing circuitry by virtue of the port to which the user connects the electrodes; and (b) a processing unit connected to the user input for receiving the patient-specific information, wherein the processing unit is configured to automatically
 (1) determine a patient type based on the patient-specific information; and
 (2) communicate the patient type determination to the defibrillator.

33. The user interface of claim 32, wherein one port is designated for connecting the electrodes to a pediatric patient and another port is designated for connecting the electrodes to an adult patient.

34. An automated external defibrillator that delivers defibrillation therapy and records event data in a memory, comprising:

(a) electrodes that are adapted for placement on a patient;
(b) a pulse generator connected to the electrodes that delivers a defibrillation pulse to the patient;
(c) processing circuitry connected to the pulse generator that controls the defibrillation pulse delivery; and
(d) a memory connected to the processing circuitry; wherein the processing circuitry is configured to automatically
 (1) collect first data pertaining to identification of the type of patient connected to the electrodes;
 (2) collect second data pertaining to evaluation and delivery of defibrillation therapy to the patient; and
 (3) record the first and second data as event data in the memory.

35. The automated external defibrillator of claim 34, further comprising a user interface that includes a user input connected to the processing circuitry, the user interface enabling a user of the defibrillator to enter patient-specific information into the defibrillator, and wherein the processing circuitry is configured to collect said first data by determining the type of patient based on the patient-specific information entered by the user.

36. The automated external defibrillator of claim 35, wherein the determined patient type is selected from the group consisting of adult, pediatric, and infant patient types.

37. The automated external defibrillator of claim 35, wherein the user interface includes a user output that prompts the user to enter the patient-specific information, said patient-specific information being entered by user interaction with the user input during a time period in relation to the prompt.

38. The automated external defibrillator of claim 37, wherein the user input enters different patient-specific information depending on the time period in which the user interacts with the user input.

39. The automated external defibrillator of claim 35, wherein the user input comprises a patient selection control that the user may manipulate to identify the patient type.

40. The automated external defibrillator of claim 35, wherein the patient-specific information entered by the user reflects an approximate age of the patient.

41. The automated external defibrillator of claim 35, wherein the patient-specific information entered by the user reflects an approximate weight of the patient.

42. The automated external defibrillator of claim 35, wherein the processing circuitry is further configured to determine a defibrillation pulse dosage to be delivered to the patient based on the patient type determination.

43. The automated external defibrillator of claim 35, wherein the processing circuitry is further configured to determine a defibrillation therapy protocol based on the patient type determination.

44. The automated external defibrillator of claim 35, wherein the user input is comprised of two or more separate ports in the defibrillator for connecting the electrodes to the defibrillator, and wherein patient-specific information is communicated by the user to the processing circuitry by virtue of the port to which the user connects the electrodes.

45. The automated external defibrillator of claim 44, wherein one port is designated for connecting the electrodes to a pediatric patient and another port is designated for connecting the electrodes to an adult patient.

46. The automated external defibrillator of claim 35, wherein the user input is comprised of a port that receives information from an external device, and wherein the patient-specific information is communicated to the defibrillator from the external device.

47. The automated external defibrillator of claim 49, wherein the port is a wireless communication port that receives information from the external device via wireless transmission.

48. The automated external defibrillator of claim 35, wherein the user input is comprised of a microphone and voice recognition circuitry capable of receiving and processing user speech, and wherein the patient-specific information is recognized and entered into the defibrillator from the user's speech.

49. The automated external defibrillator of claim 34, wherein the user input comprises a variable-length element that is extendable from the defibrillator or from a separate device, and wherein the patient-specific information is entered by the user by extending said element to approximate a physical distance related to the patient.

50. The automated external defibrillator of claim 49, wherein the physical distance is related to a height of the patient.

51. The automated external defibrillator of claim 49, wherein the physical distance is related to a length of a limb of the patient.

52. The automated external defibrillator of claim 34, wherein the processing circuitry is further connected to the electrodes and is further configured to collect the first data pertaining to identification of the patient type by detecting the configuration of the electrodes placed on the patient.

53. The automated external defibrillator of claim 52, wherein the electrodes include an indicator capable of detection by the processing circuitry of the defibrillator that indicates the configuration of the electrodes.

54. A method comprising:
receiving patient-specific information representing the magnitude of a physical attribute of a patient via a user interface that is manipulable by the user to enter the information; and
determining a patient type based on the patient-specific information received; and
causing a pulse generator to deliver a defibrillation pulse to the patient in accordance with the patient type determination.

55. The method of claim 54, further comprising prompting a user to enter the patient-specific information.

56. The method of claim 54, further comprising:
determining a defibrillation pulse dosage based on the patient type determination; and
causing the pulse generator to deliver the defibrillation pulse to the patient in accordance with the determined dosage.

57. The method of claim 54, further comprising:
determining a defibrillation therapy protocol based on the patient type determination; and
causing the pulse generator to deliver the defibrillation pulse to the patient in accordance with the determined protocol.

58. The method of claim 54, wherein receiving the patient-specific information comprises receiving the patient-specific information via an extendable variable-length element extended by a user to approximate a distance related to the patient.

59. The method of claim 54, further comprising receiving the patient-specific information via two or more separate ports, and determining the patient type based on the port which a user connects electrodes.

60. The method of claim 54, further comprising receiving the patient-specific information via wireless transmission from an external device.

61. The method of claim 54, further comprising:
collecting first data about the patient pertaining to identification of the type of patient;
collecting second data pertaining to evaluation and delivery of defibrillation therapy to the patient; and
recording the first and second data as event data in a memory.

62. An automated external defibrillator comprising:
electrodes for placement on a patient;
a pulse generator, connected to the electrodes, that delivers a defibrillation pulse to the patient;
a port that connects the electrodes to the pulse generator, and
a user interface that receives patient-specific information representing the magnitude of a physical attribute of a patient; and
processing circuitry that determines a patient type based on the patient-specific information, and causes the pulse generator to deliver a defibrillation pulse to the patient in accordance with the patient type determination.

63. The defibrillator of claim 62, further comprising a user interface to prompt the user to enter the patient-specific information.

64. The defibrillator of claim 62, wherein the processing circuitry determines a defibrillation pulse dosage based on the patient type determination, and causes the pulse generator to deliver the defibrillation pulse to the patient in accordance with the determined dosage.

65. The defibrillator of claim 62, wherein the processing circuitry determines a defibrillation therapy protocol based on the patient type determination, and causes the pulse generator to deliver the defibrillation pulse to the patient in accordance with the determined protocol.

66. The defibrillator of claim 62, further comprising an extendable variable-length element extended by a user to approximate a distance related to the patient, wherein the distance forms at least part of the patient-specific information.

67. The defibrillator of claim 62, further comprising two or more separate ports to receive electrodes, wherein the patient type is determined based on the port to which a user connects electrodes.

68. The defibrillator of claim 62, further comprising a receiver to receive the patient-specific information via wireless transmission from an external device.

69. The defibrillator of claim 62, wherein the processing circuitry collects first data about the patient pertaining to identification of the type of patient, collects second data pertaining to evaluation and delivery of defibrillation therapy to the patient, and records the first and second data as event data in a memory.

70. A method comprising:
receiving a user selection of one of two or more separate ports to connect electrodes to the defibrillator, wherein one of the ports is designated for a pediatric patient and another port is designated for an adult patient;
determining a patient type based on selection of one of the ports byte user; and
causing the pulse generator to deliver a defibrillation pulse to the patient in accordance with the patient type determination.

71. An automated external defibrillator comprising:
electrodes for placement on a patient;
a pulse generator, connected to the electrodes, that delivers a defibrillation pulse to the patient;
a user input including two or more separate ports to connect the electrodes to the defibrillator, wherein one of the ports is designated for a pediatric patient and another port is designated for an adult patient;
processing circuitry that determines a patient type based on selection of one of the ports by the user, and causes the pulse generator to deliver a defibrillation pulse to the patient in accordance with the patient type determination.

* * * * *

UNITED STATES PATENT AND TRADEMARK OFFICE
CERTIFICATE OF CORRECTION

PATENT NO. : 6,990,373 B2 Page 1 of 1
APPLICATION NO. : 10/121442
DATED : January 24, 2006
INVENTOR(S) : Cynthia P. Jayne et al.

It is certified that error appears in the above-identified patent and that said Letters Patent is hereby corrected as shown below:

In column 11, line 63, in Claim 12, delete "wit" and insert -- with --, therefor.

In column 12, line 9, in Claim 14, delete "defibrillator," and insert -- defibrillator; --, therefor.

In column 12, line 38, in Claim 17, delete "far" and insert -- for --, therefor.

In column 16, line 36, in Claim 59, delete "port" and insert -- port to --, therefor.

In column 18, line 52-53, in Claim 62, delete "generator, and" and insert -- generator; --, therefor.

In column 18, line 7, in Claim 70, delete "byte" and insert -- by the --, therefor.

Signed and Sealed this

Twenty-third Day of March, 2010

David J. Kappos
*Director of the United States Patent and Trademark Office*